US011650142B2

(12) United States Patent
Suyama

(10) Patent No.: US 11,650,142 B2
(45) Date of Patent: May 16, 2023

(54) LOGGING SYSTEM INCLUDING IMPROVED STRENGTH OF TREE MEASURING

(71) Applicant: TOYOTA JIDOSHA KABUSHIKI KAISHA, Toyota (JP)

(72) Inventor: Kazuo Suyama, Tokyo (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 115 days.

(21) Appl. No.: 17/365,547

(22) Filed: Jul. 1, 2021

(65) Prior Publication Data

US 2022/0107253 A1 Apr. 7, 2022

(30) Foreign Application Priority Data

Oct. 6, 2020 (JP) .............................. JP2020-169288

(51) Int. Cl.
*G01N 3/08* (2006.01)
*G01N 33/00* (2006.01)

(52) U.S. Cl.
CPC ........... *G01N 3/08* (2013.01); *G01N 33/0098* (2013.01)

(58) Field of Classification Search
None
See application file for complete search history.

(56) References Cited

U.S. PATENT DOCUMENTS

| 4,574,854 A | * | 3/1986 | Lindblom | ............ A01G 23/097 144/24.13 |
| 4,838,328 A | * | 6/1989 | Herolf | .................... A01G 23/08 30/379.5 |
| 2002/0113212 A1 | | 8/2002 | Meglen et al. | |
| 2020/0307978 A1 | | 10/2020 | Suyama et al. | |

FOREIGN PATENT DOCUMENTS

| JP | 2008-109918 A | | 5/2008 |
| JP | 2008109918 | * | 5/2008 |
| WO | 2020/153848 A1 | | 7/2020 |

* cited by examiner

*Primary Examiner* — Lisa M Caputo
*Assistant Examiner* — Nigel H Plumb
(74) *Attorney, Agent, or Firm* — Sughrue Mion, PLLC

(57) ABSTRACT

A measuring system for reducing the effort necessary to measure tree strength that includes support posts, a winding device configured to wind a cable supported by the support posts, a winding device configured to wind the cable, a hoisting device coupled to the cable and configured to move in air when the cable is wound by the winding device, and a measuring device hung from the hoisting device and configured to measure the strength of a tree.

7 Claims, 6 Drawing Sheets

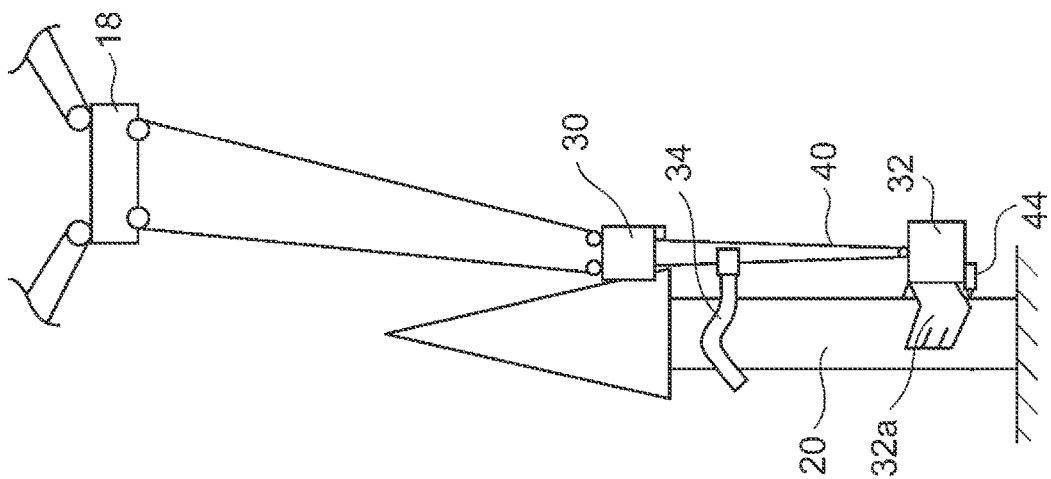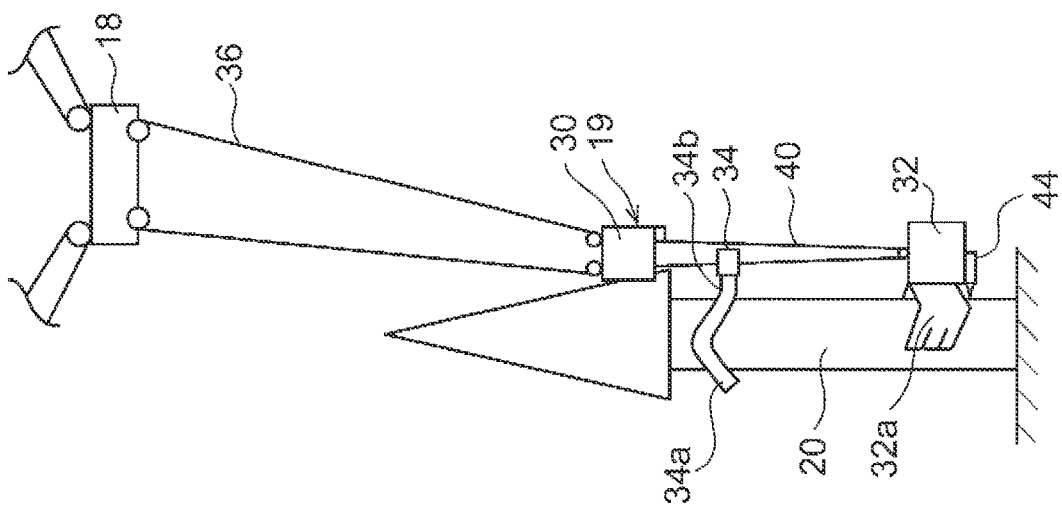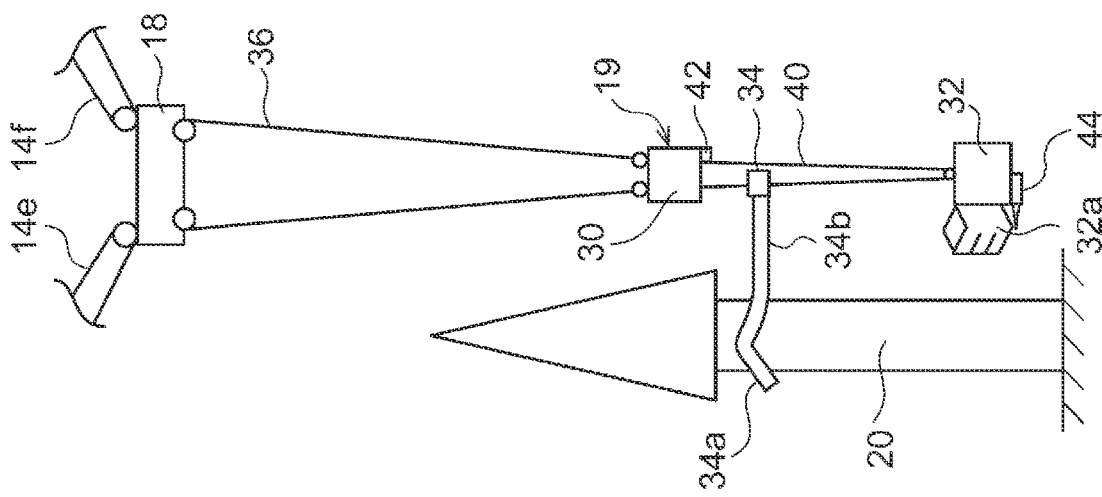

LOGGING SYSTEM INCLUDING IMPROVED STRENGTH OF TREE MEASURING

CROSS-REFERENCE TO RELATED APPLICATION

This application claims priority to Japanese Patent Application No. 2020-169288 filed on Oct. 6, 2020, incorporated herein by reference in its entirety.

BACKGROUND

1. Technical Field

The disclosure relates to a technology for measuring the strength of a tree by using cables.

2. Description of Related Art

Japanese Unexamined Patent Application Publication No. 2008-109918 (JP 2008-109918 A) describes a thinned wood transport system that transports thinned wood from a logging site to an unloading site. The thinned wood transport system includes a tower yarder placed near the unloading site on a work road, a first winch installed in the tower yarder to wind a first wire, a second winch installed in the tower yarder to wind a second wire, a plurality of pulleys coupled in the middle of a traveling route of the second wire to change a traveling direction of the second wire, a loading tool that hooks thinned wood, and a plurality of zigzag pulleys coupled in the middle of a traveling route of the loading tool to change the traveling direction of the loading tool.

SUMMARY

In measuring the strength of a tree, when a worker moves to the position of a measurement object for measurement, it is not easy to move to the measurement object when the measurement object is in a forest or the like, and the effort of the worker increases.

The disclosure provides a technology for reducing an effort to measure the strength of a tree.

An aspect of the disclosure relates to a measuring system. The measuring system includes a plurality of support posts, a cable supported by the support posts, a winding device configured to wind the cable, a hoisting device coupled to the cable and configured to move in an air when the cable is wound by the winding device, and a measuring device hung from the hoisting device and configured to measure a strength of a tree.

Another aspect of the disclosure relates to an overhead moving device hung from a cable supported by support posts and configured to move in an air when the cable is wound. The overhead moving device includes a holding device configured to hold a logged tree and transport the tree by winding the cable, and a measuring device attached to the holding device and configured to measure a strength of a tree.

Further another aspect of the disclosure relates to a measuring method. The measuring method uses a measuring system that includes a winding device configured to wind a cable supported by support posts, a hoisting device coupled to the cable and configured to move in an air when the cable is wound by the winding device, and a measuring device hung from the hoisting device. The measuring method includes sticking a pair of measuring terminals of the measuring device into a tree, and measuring a strength of the tree by detecting an output wave, output from one of the measuring terminals, with the other one of the measuring terminals.

According to the aspects of the disclosure, it is possible to provide a technology for reducing an effort to measure the strength of a tree.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 4A is a view showing a state where the hoisting device is positioned near a tree and the holding device is lowered to a position of a proximal side of the tree;

FIG. 4B is a view showing a state where the holding device is close to the tree;

FIG. 4C is a view showing a state where the holding device is holding the tree;

DETAILED DESCRIPTION OF EMBODIMENTS

Figure 1:
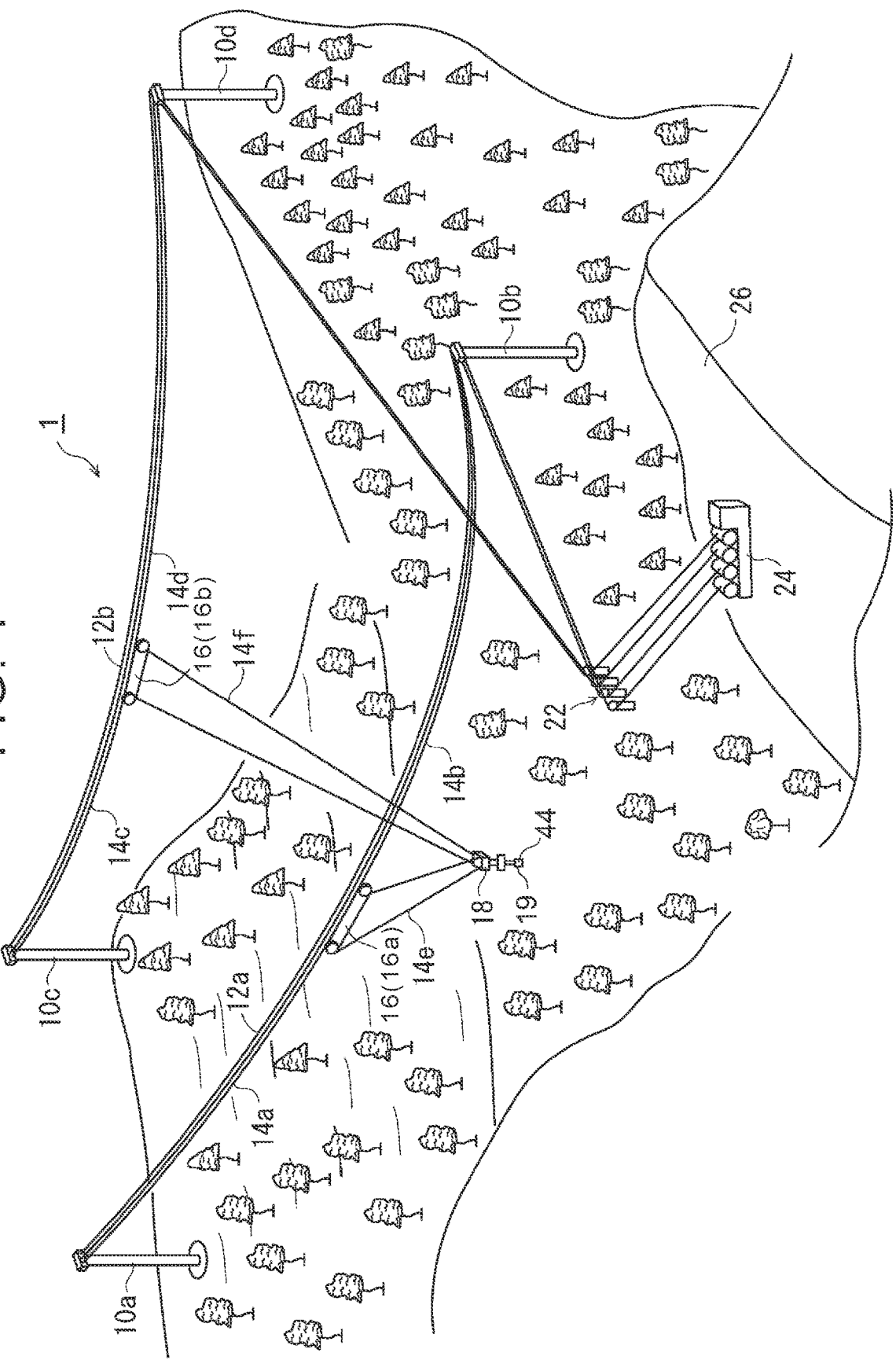
FIG. 1 is a view for illustrating a cable use system.

FIG. 1 is a view for illustrating a cable use system 1. The cable use system 1 includes a first support post 10a, a second support post 10b, a third support post 10c, a fourth support post 10d (each will be referred to as support post 10 when they are not distinguished from one another), a first main cable 12a, a second main cable 12b (each will be referred to as main cables 12 when they are not distinguished from each other), a first operation cable 14a, a second operation cable 14b, a third operation cable 14c, a fourth operation cable 14d, a fifth operation cable 14e, a sixth operation cable 14f (each will be referred to as operation cable 14 when they are not distinguished from one another), a first moving device 16a, a second moving device 16b (each will be referred to as moving device 16 when they are not distinguished from each other), a hoisting device 18, guide pulleys 22, a winch 24, and a measuring device 44.

The cable use system 1 is a so-called H-shaped cable use system and is capable of hoisting trees logged in a forest with the main cables 12 and the operation cables 14 stretched in the air and transporting the trees to near a yarding site 26. Thus, trees are transported from a forest even when there is no road.

The cable use system 1 includes the measuring device 44, so the cable use system 1 is capable of measuring the strength of a tree and functions as a measuring system. The strength of a tree is derived by measuring the Young's modulus of a tree. The strength of a tree may be the Young's modulus or may be an index value derived based on the Young's modulus. As the strength of a tree increases, strength against bending, compression, and the like increases, with the result that the tree becomes more difficult to deform. When the strengths of trees are obtained, selective logging according to the uses of materials is possible.

When the strength of a tree is high, the tree is used for a pillar or a wall. When the strength of a tree is low, the tree is subject to thinning.

The four support posts 10 are erected at positions suitable for installation and determined based on the arrangement of standing trees and the position of the yarding site 26. The size of each support post 10 is set to the range of about five meters to 10 meters according to the size and the like of the cable use system 1.

Each of the main cables 12 and the operation cables 14 is fixed to the support post 10 as a cable or wrapped around a pulley of the support post 10. The first main cable 12a is fixed to the first support post 10a and the second support post 10b. The second main cable 12b is fixed to the third support post 10c and the fourth support post 10d. The first main cable 12a and the second main cable 12b function as rails in the air. The first main cable 12a and the second main cable 12b are provided so as not to intersect with each other. The length of each main cable 12 is set to a range from about 300 meters to about 2000 meters.

The operation cable 14 functions as a running cable to be wound by the moving device 16 or the winch 24. The first operation cable 14a, the second operation cable 14b, the third operation cable 14c, and the fourth operation cable 14d are routed through the pulleys respectively provided at the support posts 10. One end of each of the first operation cable 14a, the second operation cable 14b, the third operation cable 14c, and the fourth operation cable 14d is coupled to an associated one of the moving devices 16, and the other end is coupled to the winch 24. The first operation cable 14a is routed from the winch 24 and coupled to the first moving device 16a via the second support post 10b and the first support post 10a. The second operation cable 14b is routed from the winch 24 and coupled to the first moving device 16a via the second support post 10b. The third operation cable 14c is routed from the winch 24 and coupled to the second moving device 16b via the fourth support post 10d and the third support post 10c. The fourth operation cable 14d is routed from the winch 24 and coupled to the second moving device 16b via the fourth support post 10d. The fifth operation cable 14e and the sixth operation cable 14f are each coupled to the hoisting device 18 and an associated one of the moving devices 16.

The moving devices 16 are respectively supported by the main cables 12 and are movable along the main cables 12. The first operation cable 14a, the second operation cable 14b, and the fifth operation cable 14e are coupled to the first moving device 16a. The third operation cable 14c, the fourth operation cable 14d, and the sixth operation cable 14f are coupled to the second moving device 16b. The fifth operation cable 14e couples the first moving device 16a and the hoisting device 18. The sixth operation cable 14f couples the second moving device 16b and the hoisting device 18. The moving devices 16 have the function to wind and unwind the fifth operation cable 14e and the sixth operation cable 14f in accordance with a wirelessly transmitted command signal.

The hoisting device 18 is coupled to a holding device 19 by a wire for lifting and lowering. The measuring device 44 is attached to the holding device 19. The holding device 19 and the measuring device 44 are hung from the hoisting device 18. Each of the guide pulleys 22 changes the direction of the wrapped operation cable 14. The winch 24 functions as a winch to wind each of the operation cables 14 and has drums and drive sources for winding or unwinding the operation cables 14, respectively.

The operation of the cable use system 1 will be described. The winch 24 winds one of the first operation cable 14a and the second operation cable 14b and unwinds the other one to move the first moving device 16a along the first main cable 12a. In addition, the winch 24 winds one of the third operation cable 14c and the fourth operation cable 14d and unwinds the other one to move the second moving device 16b along the second main cable 12b. Thus, the hoisting device 18 is displaced along the main cables 12.

The moving devices 16 wind one of the fifth operation cable 14e and the sixth operation cable 14f and unwind the other one to cause the hoisting device 18 to move between the first moving device 16a and the second moving device 16b. Thus, the hoisting device 18 is moved in a horizontal direction within a region surrounded by the four support posts 10.

In this way, the winch 24 and the moving devices 16 function as a winding device capable of winding cables. The winding device enables the hoisting device 18 to move in the horizontal direction in the air by winding the operation cables 14 (cables).

In the configuration of the cable use system 1 shown in FIG. 1, the moving devices 16 that respectively wind the fifth operation cable 14e and the sixth operation cable 14f are respectively coupled to the main cables 12; however, the cable use system 1 is not limited to this configuration. When the fifth operation cable 14e and the sixth operation cable 14f are extended to the position of the winch 24, the winch 24 has the function to wind the moving devices 16. The winch 24 is not limited to the configuration in which individual winches are concentrated at one location. The winch 24 may be configured such that individual winches are provided one by one at the support posts 10. In this way, the winding device may be integrated or separated.

Figure 2:
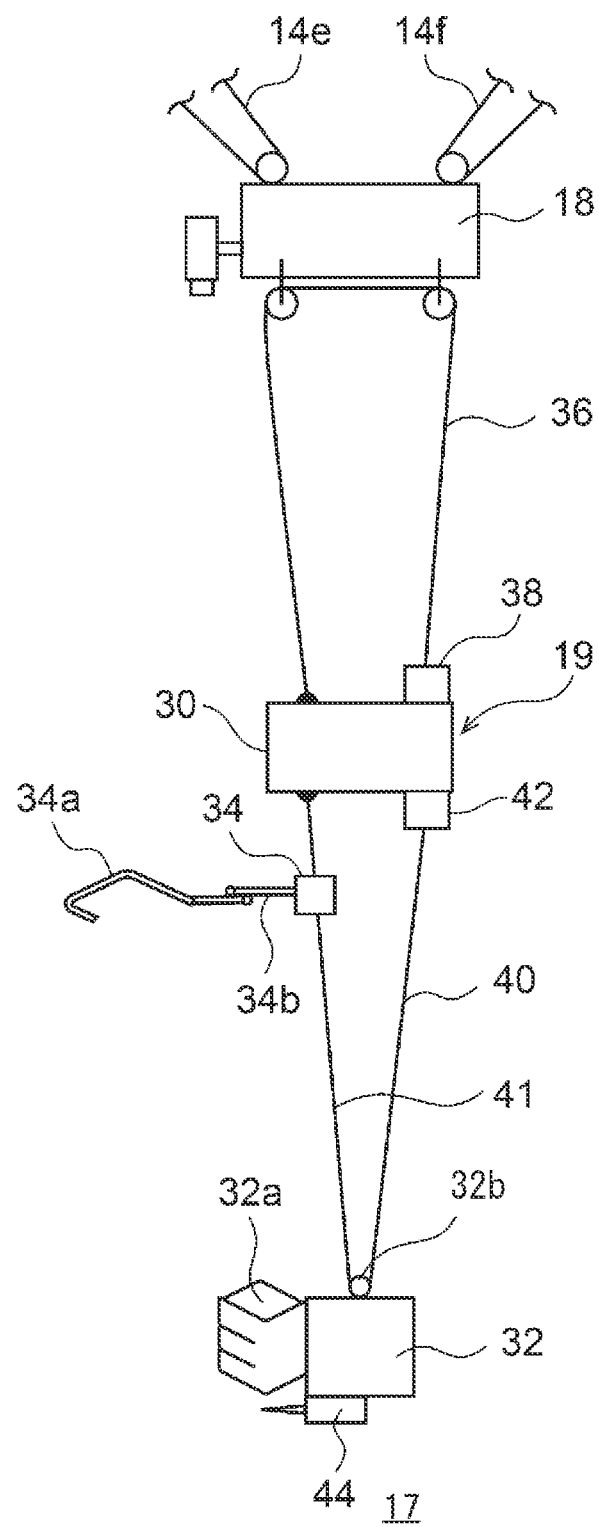
FIG. 2 is a view for illustrating a holding device and a measuring device both hung from a hoisting device.

FIG. 2 is a view for illustrating the holding device 19 and the measuring device 44 both hung from the hoisting device 18. The hoisting device 18, the holding device 19, and the measuring device 44 make up an overhead moving device 17. The overhead moving device 17 moves in the air when the cables are wound. The hoisting device 18 is coupled to the fifth operation cable 14e and the sixth operation cable 14f. The holding device 19 is hung from the hoisting device 18 by a first wire 36.

The holding device 19 includes an actuator 30, a first holding unit 32, a second holding unit 34, the first wire 36, a second wire 40, a first motor 38, and a second motor 42. The actuator 30, the first holding unit 32, the second holding unit 34, the first motor 38, and the second motor 42 are remotely controllable and controlled by a controller (described later).

One end of the first wire 36 is fixed to the actuator 30, and the other end side of the first wire 36 is coupled to the actuator 30 so as to be wound and unwound. The first wire 36 is coupled to the hoisting device 18 via pulleys. The first motor 38 is provided on the actuator 30 and is capable of winding and unwinding the first wire 36. The holding device 19 moves in an up and down direction with respect to the hoisting device 18 by driving the first motor 38.

The first holding unit 32 and the second holding unit 34 are hung by the second wire 40 from the actuator 30. One end of the second wire 40 is fixed to the actuator 30, the middle part of the second wire 40 is coupled to the first holding unit 32 via a pulley 32b provided on the first holding unit 32, and the other end of the second wire 40 is coupled to the actuator 30 such that the second wire 40 can be wound and unwound. The second motor 42 is provided on the actuator 30 and is capable of winding and unwinding the second wire 40. The first holding unit 32 moves in the up and down direction with respect to the actuator 30 by driving the second motor 42.

The first holding unit 32 includes a pair of clamping portions 32a and the pulley 32b. The pair of clamping portions 32a can be driven to close and open and clamps the outer periphery of a tree. The pair of clamping portions 32a approaches a tree in an open state and closes to clamp the tree.

The second holding unit 34 is a manipulator and is fixed to the second wire 40. The second holding unit 34 is provided between the actuator 30 and the first holding unit 32 and is located above the first holding unit 32. The second holding unit 34 includes a grip portion 34a and an arm portion 34b. The grip portion 34a is located at the distal end portion of the second holding unit 34 and grips the outer periphery of a tree. The arm portion 34b has a plurality of joints. The arm portion 34b is capable of bringing the grip portion 34a close to a tree by moving in a direction away from the second wire 40. After the grip portion 34a holds the tree, the arm portion 34b contracts to bring the grip portion 34a close to the second wire 40. Thus, the first holding unit 32 approaches the tree. The first holding unit 32 and the second holding unit 34 are capable of holding a logged tree and transport the tree in the air through winding of the winding device.

The holding device 19 is capable of moving the actuator 30 up and down by driving the first motor 38 and is capable of moving the first holding unit 32 up and down by driving the second motor 42. Thus, the first holding unit 32 and the second holding unit 34 each can be caused to hold a tree at an adequate position.

The measuring device 44 is provided on the lower part of the first holding unit 32. The measuring device 44 is provided so as to be slidable with respect to the first holding unit 32. Thus, the measuring terminals of the measuring device 44 can be stuck into a tree.

Figure 3:
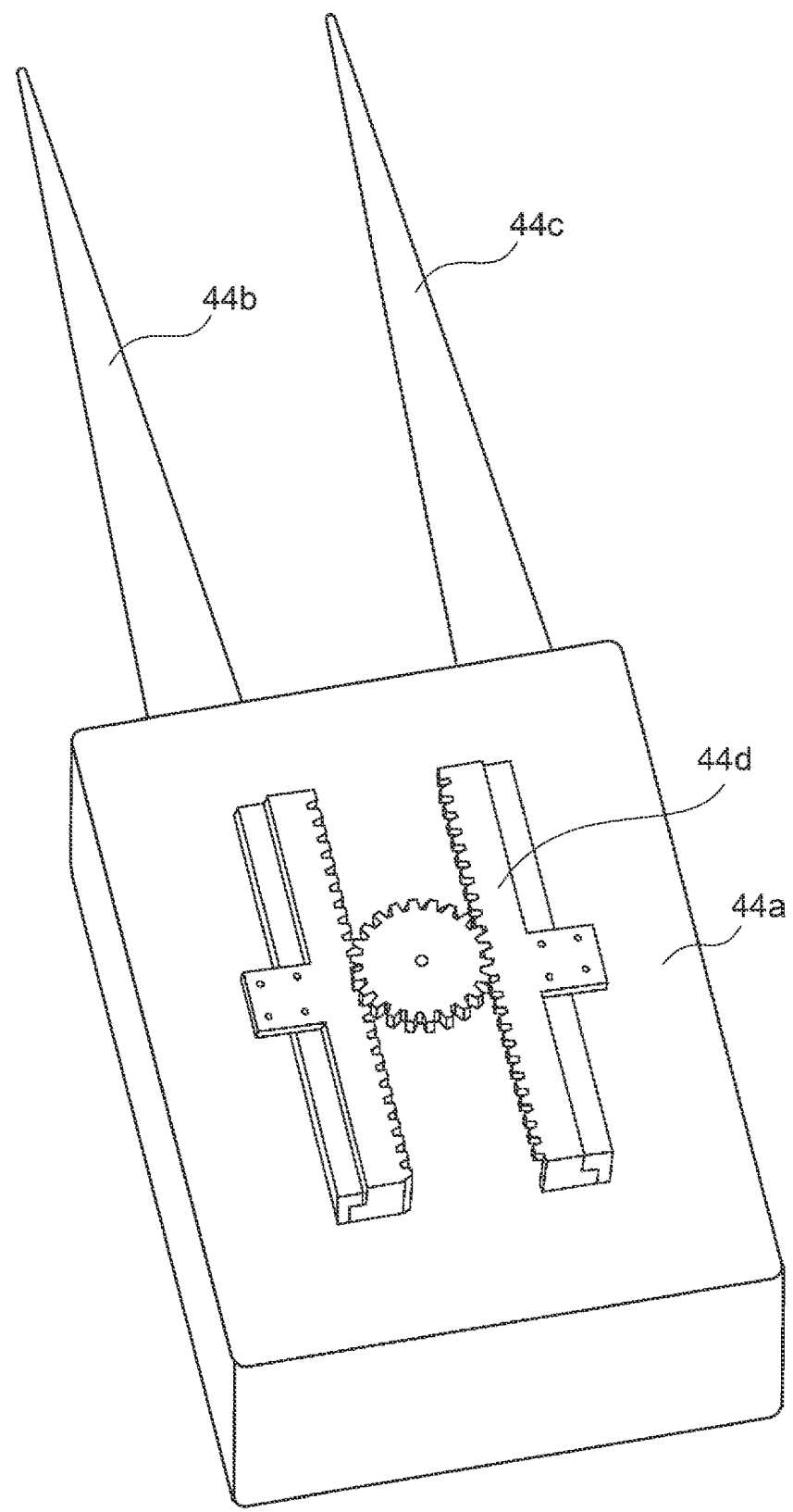
FIG. 3 is a perspective view of the measuring device.

FIG. 3 is a perspective view of the measuring device 44. The measuring device 44 measures the strength of a tree with an ultrasonic wave. The measuring device 44 includes a body portion 44a, a first measuring terminal 44b, a second measuring terminal 44c, and a slide mechanism 44d.

The body portion 44a is formed in a box shape and contains an electronic circuit for measurement, a power supply, and the like inside. The first measuring terminal 44b and the second measuring terminal 44c (each will be simply referred to as measuring terminal when they are not distinguished from each other) each are formed in a rod shape and protrude from the body portion 44a parallel to each other. The distal end of each of the first measuring terminal 44b and the second measuring terminal 44c is formed in a tapered shape.

The space between the first measuring terminal 44b and the second measuring terminal 44c is set to a range from 15 centimeters to 25 centimeters. The protruding length of each of the first measuring terminal 44b and the second measuring terminal 44c may be set to a range from 20 centimeters to 40 centimeters. The size of each measuring terminal is not limited to the above-described size.

The slide mechanism 44d enables the measuring device 44 to slide with respect to the first holding unit 32. The slide mechanism 44d slides in the longitudinal direction of the first measuring terminal 44b and the second measuring terminal 44c. The slide mechanism 44d includes a pair of rack gears and a pinion gear. The rack gears are fixed to the first holding unit 32. The pinion gear is rotatably supported by the body portion 44a and is rotated by a motor contained in the body portion 44a. The slide mechanism 44d moves the first measuring terminal 44b and the second measuring terminal 44c along the horizontal direction.

As a result of the slide of the slide mechanism 44d, the first measuring terminal 44b and the second measuring terminal 44c stick into a tree. The protruding length of each of the first measuring terminal 44b and the second measuring terminal 44c is set such that, when the first measuring terminal 44b and the second measuring terminal 44c are stuck in the tree, the heartwood of the tree is located between the first measuring terminal 44b and the second measuring terminal 44c.

In a state where the first measuring terminal 44b and the second measuring terminal 44c are stuck in the tree, the body portion 44a outputs a sonic wave from the first measuring terminal 44b and causes the second measuring terminal 44c to detect the sonic wave. The measuring device 44 derives the strength of the tree based on a detection result of the second measuring terminal 44c. In this way, the strength of the tree is derived from the propagation speed of sonic wave in the tree.

The installation position of the measuring device 44 on the first holding unit 32 is set such that, when the slide mechanism 44d is caused to slide in a state where the clamping portions 32a is holding a tree, the center of the tree is located between the first measuring terminal 44b and the second measuring terminal 44c or between the extended lines of the first measuring terminal 44b and second measuring terminal 44c. For example, the measuring device 44 is installed at a position that overlaps the proximal ends of the pair of clamping portions 32a in the up and down direction.

FIG. 4A, FIG. 4B, and FIG. 4C are views illustrating the operation of the cable use system 1 for measuring the strength of a tree. FIG. 4A shows a state where the hoisting device 18 is positioned near a tree and the holding device 19 is lowered to a position of a proximal side of the tree. The grip portion 34a of the second holding unit 34 is holding the tree.

Control to lower the holding device 19 and control to cause the second holding unit 34 to hold the tree may be executed by a program provided in advance or may be executed by operation of an operator. Alternatively, control of the cable use system 1 may be a combination of a program and operation of an operator. For example, an operator controls the cable use system 1 while watching an image transmitted from a camera provided at the hoisting device 18, the actuator 30, or the like.

FIG. 4B shows a state where the arm portion 34b is driven to contract and the first holding unit 32 is close to the tree. The holding device 19 shifts in the horizontal direction with respect to the hoisting device 18. When the first holding unit 32 is close to the tree, the pair of clamping portions 32a clamps the proximal side of the tree. The first holding unit 32 holds the proximal side of the tree. The second holding unit 34 holds part of the tree above the first holding unit 32. The second holding unit 34 may hold the middle part of a tree or may hold a part above a half of the height of a tree. Thus, the first holding unit 32 and the second holding unit 34 hold the tree at two points. The space between the first holding unit 32 and the second holding unit 34 may be determined according to the height of a tree.

FIG. 4C shows a state where, while the first holding unit 32 and the second holding unit 34 are holding a tree, the slide mechanism 44d of the measuring device 44 is driven to cause the first measuring terminal 44b and the second measuring terminal 44c to project toward the tree and stick into the tree. The measuring device 44 measures the strength of the tree by outputting a sonic wave from the first measuring terminal 44*b*. After measurement, the slide mechanism 44*d* is driven to retract and pull out the first measuring terminal 44*b* and the second measuring terminal 44*c* from the tree.

In this way, to measure the strength of a tree, holding the tree by the holding device 19, sticking the measuring terminals into the tree, measurement through output of a sonic wave, and pulling out the measuring terminals are performed. The measured strength of the tree is transmitted to a server 72 of a data center together with position information and stored.

In this way, the strength of a standing tree can be remotely measured and does not need to be measured on site actually, so the effort of a worker is reduced. When the strengths of trees are obtained, selective logging according to demands is possible.

Measurement of the strength of a tree may be performed just before logging or may be performed at intervals of a predetermined period, such as every other year. The measuring device 44 may perform measurement at multiple heights for a tree. When measurement is performed at multiple points of a tree, measurement accuracy is increased.

Figure 5:
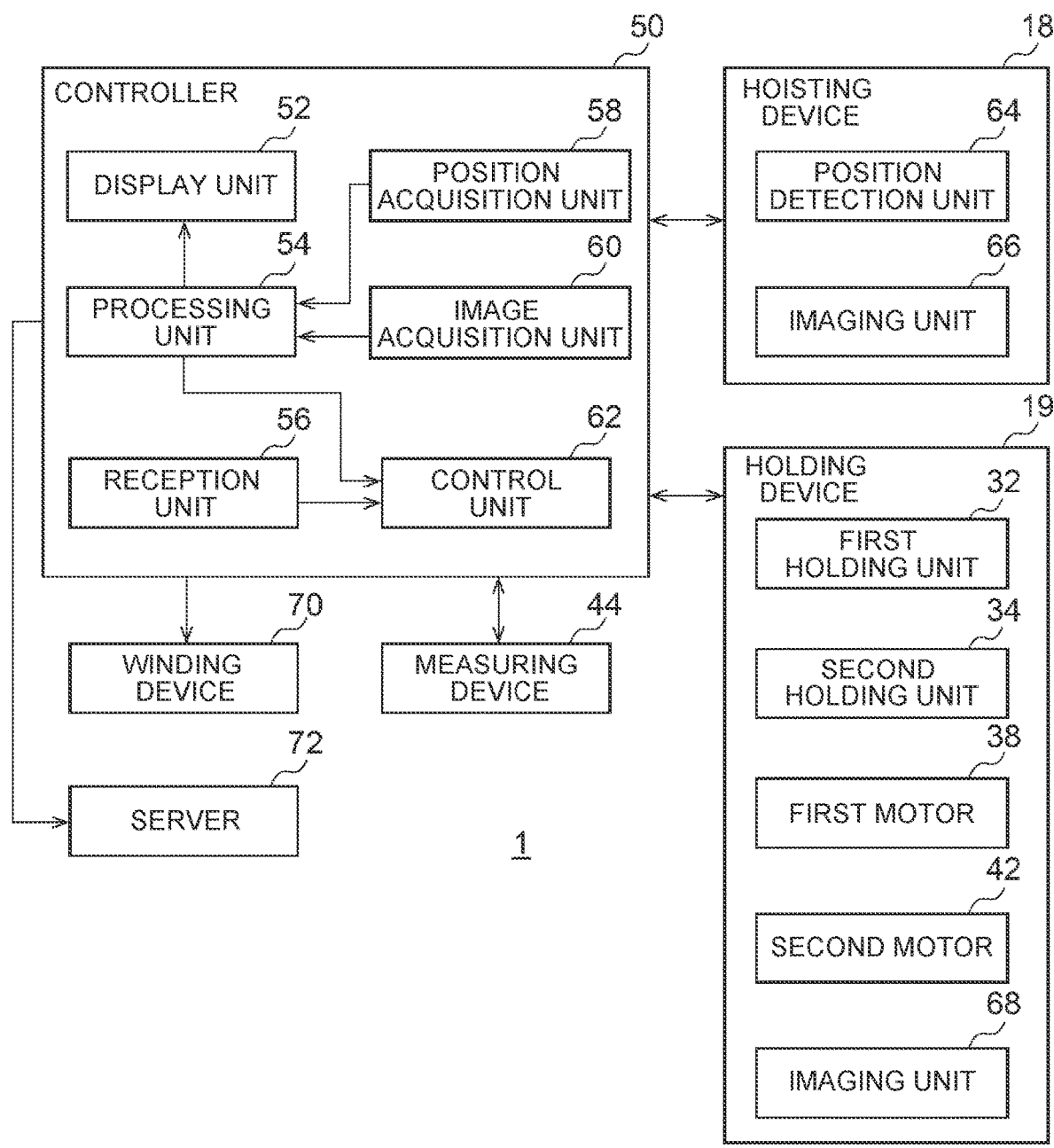
FIG. 5 is a diagram showing the schematic configuration of the cable use system.

FIG. 5 shows the functional configuration of the cable use system 1. The controller 50 is provided in a control room and enables the winding device 70, the hoisting device 18, the holding device 19, the actuator 30, and the measuring device 44 to be controlled remotely. The controller 50 is capable of communicating with the server 72. The winding device 70 includes the winch 24 and the moving devices 16 and is capable of communicating with the controller 50.

The hoisting device 18 includes a position detection unit 64 and an imaging unit 66 and is capable of communicating with the controller 50. The position detection unit 64 detects information about the position of the hoisting device 18 by using a satellite positioning system. The imaging unit 66 is a camera provided at the hoisting device 18. The imaging unit 66 mainly takes an image below the hoisting device 18 and detects a taken image containing the holding device 19.

The holding device 19 includes an imaging unit 68 in addition to the first holding unit 32, the second holding unit 34, the first motor 38, and the second motor 42. The imaging unit 68 is provided at the actuator 30 and takes an image of the first holding unit 32 and an image of the second holding unit 34. The actuator 30, the first holding unit 32, and the second holding unit 34 may be capable of communicating with the controller 50. Alternatively, any one of the actuator 30, the first holding unit 32 and the second holding unit 34 may have a communication function, and the actuator 30, the first holding unit 32, and the second holding unit 34 may be connected by wire or near field communication. In any case, the components of the holding device 19 are capable of exchanging information with the controller 50. The measuring device 44 may wirelessly communicate with the controller 50 or may communicate with the controller 50 by using the communication function of the holding device 19.

The controller 50 includes a display unit 52, a processing unit 54, a reception unit 56, a position acquisition unit 58, an image acquisition unit 60, and a control unit 62. The position acquisition unit 58 acquires information about the position of the hoisting device 18 from the hoisting device 18. The image acquisition unit 60 acquires taken images from the imaging unit 66 and the imaging unit 68, respectively. The imaging unit 68 takes not only the images of the first holding unit 32 and second holding unit 34 but also the image of the measuring device 44. In addition to the imaging unit 66 and the imaging unit 68, further another imaging unit may be provided at the measuring device 44. The reception unit 56 is a touch panel or mechanical controller and receives operation of an operator.

The processing unit 54 generates command information for causing the hoisting device 18 to move to a predetermined position based on the information about the position of the hoisting device 18 and the taken images of the hoisting device 18 and holding device 19. For example, the processing unit 54 generates command information for causing the hoisting device 18 to move to the position of the tree planned to be measured. The command information generated by the processing unit 54 is sent to the control unit 62, and control according to the command information is executed.

The processing unit 54 generates a display image to be displayed on the display unit 52, based on the information about the position of the hoisting device 18 and the taken images of the hoisting device 18 and holding device 19. An operator operates the hoisting device 18 and the holding device 19 while watching the information about the position of the hoisting device 18 and the taken images of the hoisting device 18 and holding device 19, displayed on the display unit 52.

When the holding device 19 completes holding a tree, the processing unit 54 generates command information for causing the measuring device 44 to stick the measuring terminals into the tree, causing the measuring device 44 to perform measurement and causing the measuring device 44 to pull out the measuring terminals, and causes the measuring device 44 to measure the strength of the tree.

In this way, the processing unit 54 automatically moves the hoisting device 18, and an operator operates the drive of the holding device 19. An operator may operate a step in which the second holding unit 34 and the first holding unit 32 hold a tree, and the processing unit 54 may automatically perform the other measuring steps. An operator may check through the display unit 52 whether the measuring device 44 is sufficiently stuck in the tree and then operate to cause the measuring device 44 to start measurement. Alternatively, the processing unit 54 may automatically perform all the tree measuring steps.

The control unit 62 controls the winding device 70, the hoisting device 18, the holding device 19, and the measuring device 44 based on command information from the processing unit 54 or operation information of an operator, input to the reception unit 56. The control unit 62 controls the winding device 70 so as to move the hoisting device 18 to a predetermined position. The control unit 62 controls the holding device 19 in accordance with operation of an operator. The control unit 62 controls the measuring device 44 in accordance with command information generated by the processing unit 54 or operation of an operator.

The processing unit 54 transmits information on the strength of a tree, measured by the measuring device 44, and information about the position of the hoisting device 18 at the time of measurement, acquired by the position acquisition unit 58, to the server 72 in association with each other. Information about the position of the hoisting device 18 at the time of measurement indicates information about the position of a tree being measured. The server 72 holds the information about the strength of the tree and the information about the position of the tree in association with each other. Thus, resource management is performed based on the strengths of trees.

Figure 6:
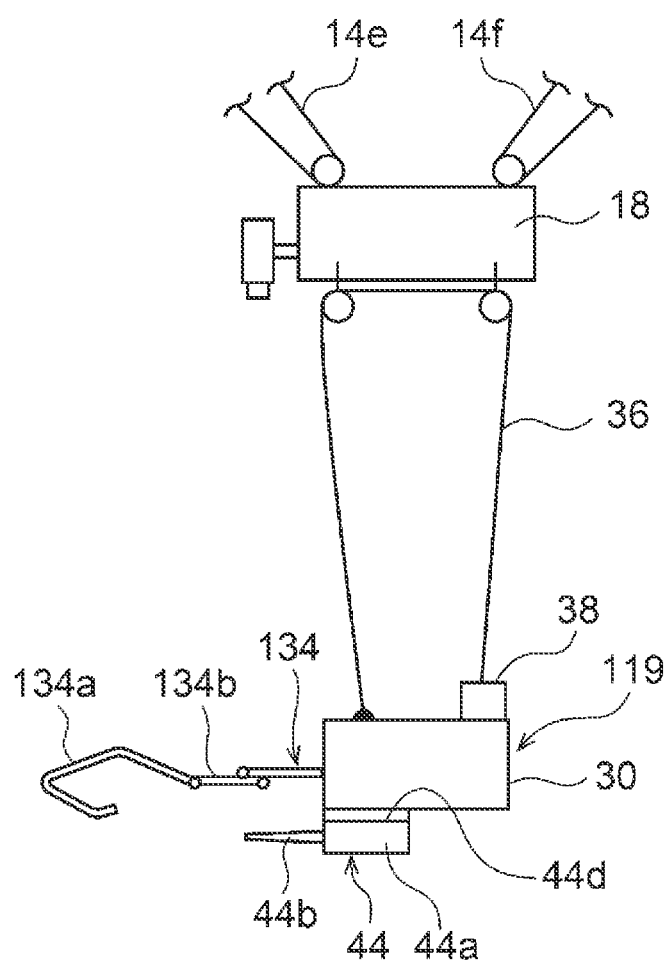
FIG. 6 is a view for illustrating a holding device and a measuring device according to a modification.

FIG. 6 is a view for illustrating a holding device 119 and the measuring device 44 according to a modification. The holding device 119 of the modification differs from the holding device 19 shown in FIG. 2 in that only one holding unit 134 is provided. The holding device 119 includes the actuator 30, the first wire 36, the first motor 38, and the holding unit 134.

The holding unit 134 is a manipulator and is provided at the actuator 30. The holding unit 134 hangs over from the actuator 30 in the horizontal direction. The holding unit 134 includes a grip portion 134a and an arm portion 134b. The grip portion 134a is located at the distal end portion of the holding unit 134 and grips the outer periphery of a tree. The arm portion 134b has a plurality of joints. The arm portion 134b is capable of bringing the grip portion 134a close to a tree by moving in a direction away from the actuator 30. After the grip portion 134a holds the tree, the arm portion 134b contracts to bring the grip portion 134a close to the actuator 30. Thus, the measuring device 44 provided at the holding unit 134 approaches the tree.

The measuring device 44 is fixed to the lower part of the actuator 30 and is hung from the hoisting device 18. The first measuring terminal 44b and the second measuring terminal 44c are capable of projecting and retracting in the horizontal direction by the slide mechanism 44d.

After the holding unit 134 holds a tree and causes the actuator 30 to approach the tree, the measuring device 44 sticks the measuring terminals into the tree for measurement. In process in which the holding unit 134 causes the actuator 30 to approach the tree, the measuring terminals of the measuring device 44 may be stuck into a tree. In this case as well, in a state where the holding unit 134 is holding a tree, the measuring terminals stick into the tree.

The disclosure is described with reference to the embodiment. It is to be understood by those skilled in the art that the embodiment is illustrative, that the embodiment may have modifications having various combinations of constituent elements and operation processes, and that the scope of the disclosure also encompasses these modifications.

The mode in which the measuring device 44 of the embodiment measures by using a sonic wave is described; however, the configuration is not limited to this mode. For example, the strength of a tree may be derived based on the propagation speed of a stress wave, obtained by sticking two measuring terminals into the tree. One of the measuring terminals outputs a stress wave, and the other measuring terminal detects the stress wave. Thus, the propagation speed of the stress wave is measured. In this mode, the pair of measuring terminals may be provided apart from each other on the upper part and lower part of the first holding unit 32. In any case, the measuring device 44 measures the strength of a tree by detecting an output wave, output from one of the measuring terminals, with the other one of the measuring terminals.

The first holding unit 32 may include a cutter portion capable of cutting a tree. In a state where the first holding unit 32 and the second holding unit 34 hold a tree, the cutter portion cuts the tree by rotating the tree along the horizontal direction. Thus, even when a tree is cut, the tree is held in the air without being felled, and then transported as it is. The cutter portion is provided on the lower part of the first holding unit 32. The measuring device 44 is provided on the upper part of the first holding unit 32. The cutter portion is a chain saw or an electrically-powered saw.

In the embodiment, the mode in which the first motor 38 for winding the first wire 36 is provided on the holding device 19 is described; however, the configuration is not limited to this mode. For example, the hoisting device 18 may include a motor for winding the first wire 36.

In the embodiment, the mode in which the pair of measuring terminals is provided in the one-unit measuring device 44 is described; however the configuration is not limited to this mode. For example, one of the pair of measuring terminals may be provided on the first holding unit 32, and the other one may be provided on the second holding unit 34.

What is claimed is:

1. A measuring system comprising:
   a plurality of support posts;
   a cable supported by the support posts;
   a winding device configured to wind the cable;
   a hoisting device coupled to the cable, the hoisting device being configured to move in air when the cable is wound by the winding device; and
   a measuring device hung from the hoisting device and configured to measure a strength of a tree.

2. The measuring system according to claim 1, further comprising a holding device hung from the hoisting device and configured to hold the tree, wherein:
   the measuring device has a measuring terminal to be stuck into the tree; and
   the measuring terminal is stuck in the tree in a state where the holding device is holding the tree.

3. The measuring system according to claim 2, wherein the holding device includes
   a grip portion configured to hold the tree, and
   an arm portion configured to bring the measuring device close to the tree in a state where the tree is held by the grip portion.

4. The measuring system according to claim 1, wherein the measuring device includes
   a pair of measuring terminals parallel to each other, and
   a slide mechanism configured to move the measuring terminals in a longitudinal direction of the measuring terminals.

5. The measuring system according to claim 1, further comprising a server configured to receive information on the strength of the tree, measured by the measuring device, wherein the server holds information on the strength of the tree and information about a position of the tree in association with each other.

6. An overhead moving device hung from a cable supported by a plurality of support posts and configured to move in-aft air when the cable is wound, the overhead moving device comprising:
   a holding device configured to hold a logged tree and transport the tree by winding the cable; and
   a measuring device attached to the holding device and configured to measure a strength of the tree.

7. A measuring method using a measuring system that includes a winding device configured to wind a cable supported by a plurality of support posts, a hoisting device coupled to the cable and configured to move in air when the cable is wound by the winding device, and a measuring device hung from the hoisting device, the measuring method comprising:
   sticking a pair of measuring terminals of the measuring device into a tree; and
   measuring a strength of the tree by detecting an output wave, output from one of the measuring terminals, with the other one of the measuring terminals.

* * * * *